United States Patent [19]
Chen

[11] Patent Number: 5,932,147
[45] Date of Patent: *Aug. 3, 1999

[54] TURBO DRIVEN AIR FRESHENER AND METHOD THEREFOR

[75] Inventor: Wen Jye Chen, Taipei Hsien, Taiwan

[73] Assignee: American Auto Accessories, Inc., Corona, N.Y.

[*] Notice: This patent is subject to a terminal disclaimer.

[21] Appl. No.: 08/893,357

[22] Filed: Jul. 16, 1997

[51] Int. Cl.[6] .................................................. B01D 47/00
[52] U.S. Cl. .................... 261/30; 261/100; 261/DIG. 65; 261/DIG. 17; 422/124; 239/56
[58] Field of Search .......................... 261/DIG. 65, 100, 261/104, 107, 84, DIG. 17; 239/53, 54, 55, 56, 57, 58, 59, 60; 422/123, 124; 55/404, 471

[56] References Cited

U.S. PATENT DOCUMENTS

| | | | |
|---|---|---|---|
| 4,523,870 | 6/1985 | Spector | 239/59 |
| 4,654,198 | 3/1987 | Berardini | 422/124 |
| 4,722,264 | 2/1988 | DeGuisseppe | 422/124 |
| 5,269,723 | 12/1993 | Bender | 239/57 |
| 5,407,642 | 4/1995 | Lord | 422/122 |
| 5,478,505 | 12/1995 | McElfresh et al. | 261/30 |
| 5,480,591 | 1/1996 | Lagneaux et al. | 261/DIG. 65 |

FOREIGN PATENT DOCUMENTS

| | | | |
|---|---|---|---|
| 1514712 | 6/1978 | United Kingdom | 422/123 |

*Primary Examiner*—Jay H. Woo
*Assistant Examiner*—Robert A. Hopkins
*Attorney, Agent, or Firm*—Robert C. Kain, Jr.

[57] ABSTRACT

The air freshener device is adapted to be mounted on a ventilation duct in a vehicle or other closed space. The housing has a front side and a back side and respective input and output air ports defined thereon. Forced air, expelled from the ventilation ducts, enters the input air ports of the housing, causes a rotatable fan to rotate and generate arcuate and, preferably rotating, air currents in the generally hollow interior space defined by the housing. An air freshener pellet is disposed within the housing and the arcuate air flow, and preferably rotatable air flow, passes over the pellet, mixes with the expelled ventilation air and is ejected from the housing via the output air port.

20 Claims, 2 Drawing Sheets

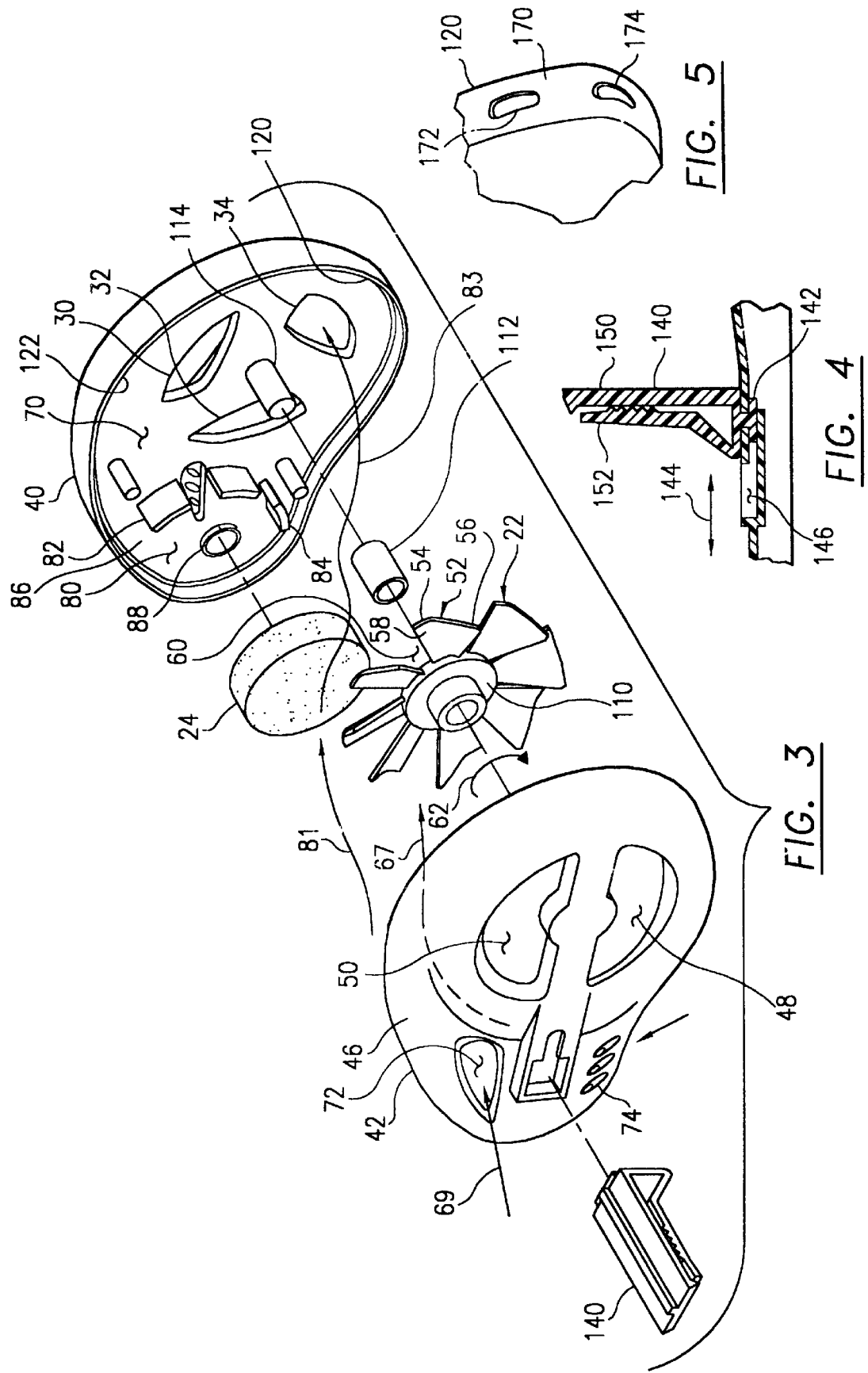

TURBO DRIVEN AIR FRESHENER AND METHOD THEREFOR

The present invention relates to an air freshener device having a fan which is driven by forced air expelled from a ventilation duct.

In certain confined areas, such as automobiles and in other vehicles, air is forced through ventilation ducts in order to cool the contained space, heat the contained space or provide fresh air piped in from outside the vehicle or other contained space. Specially with respect to a vehicle, the air in the vehicle can become stale. Odors trapped in the vehicle may be unpleasant for the driver or other passengers. Accordingly, the use of air fresheners in vehicles and in other contained spaces is common place.

OBJECTS OF THE INVENTION

It is an object of the present invention to provide an air freshener device, mounted on a ventilation duct, which freshens the air by developing rotating air currents or arcuate air currents over an air freshener pellet in the device.

It is another object of the present invention to provide an air freshener device wherein the device's housing contains a rotatable fan and an air freshener pellet and can be opened so that the air freshener pellet or carrier can be replaced or recharged.

It is an additional object of the present invention to provide multiple input air ports in the housing, some of which are located immediately adjacent the air freshener pellet, in order to maximize the distribution or off-gassing of scent by the air freshener pellet in the air circulating through the device.

It is an additional object of the present invention to provide an air freshener device which utilizes a turbine or fan that causes air to circulate within the interior of the housing carrying the air freshener pellet and to enhance the distribution of the freshened air with the air expelled from the ventilation duct.

It is an additional object of the present invention to provide a method for freshening air which generates arcuate air flow over the air freshener pellet and ejects the freshened air with the arcuate air flow into the expelled ventilation duct air.

It is another object of the present invention to provide an air freshener pellet which can be a solid pellet, a packet with a plurality of air freshener beads or small pellets or a sponge which can absorb air freshener liquid and permit that liquid to evaporate during the arcuate and rotatable air flow caused by the fan in the housing.

SUMMARY OF THE INVENTION

The air freshener device is adapted to be mounted on a ventilation duct in a vehicle or other closed space. The housing has a front side and a back side and respective input and output air ports defined thereon. Forced air, expelled from the ventilation ducts, enters the input air ports of the housing, causes a rotatable fan to rotate and generate arcuate and, preferably rotating, air currents in the generally hollow interior space defined by the housing. An air freshener pellet is disposed within the housing and the arcuate air flow, and preferably rotatable air flow, passes over the pellet, mixes with the expelled ventilation air and is ejected from the housing via the output air port.

BRIEF DESCRIPTION OF THE DRAWINGS

Further objects and advantages of the present invention can be found in the detailed description of the preferred embodiments, when taken in conjunction with the accompanying drawings in which:

FIG. 3 diagrammatically illustrates an exploded view of the air freshener device from a rearward or back side perspective;

FIG. 4 diagrammatically illustrates the clip utilized in the preferred embodiment to mount the air freshener device on the ventilation duct; and FIG. 5 diagrammatically illustrates side air ports.

DETAILED DESCRIPTION OF THE PREFERRED EMBODIMENT

The present invention relates to an air freshener device to be mounted on a ventilation duct in a vehicle or other confined space and a method therefor.

Figure 1:
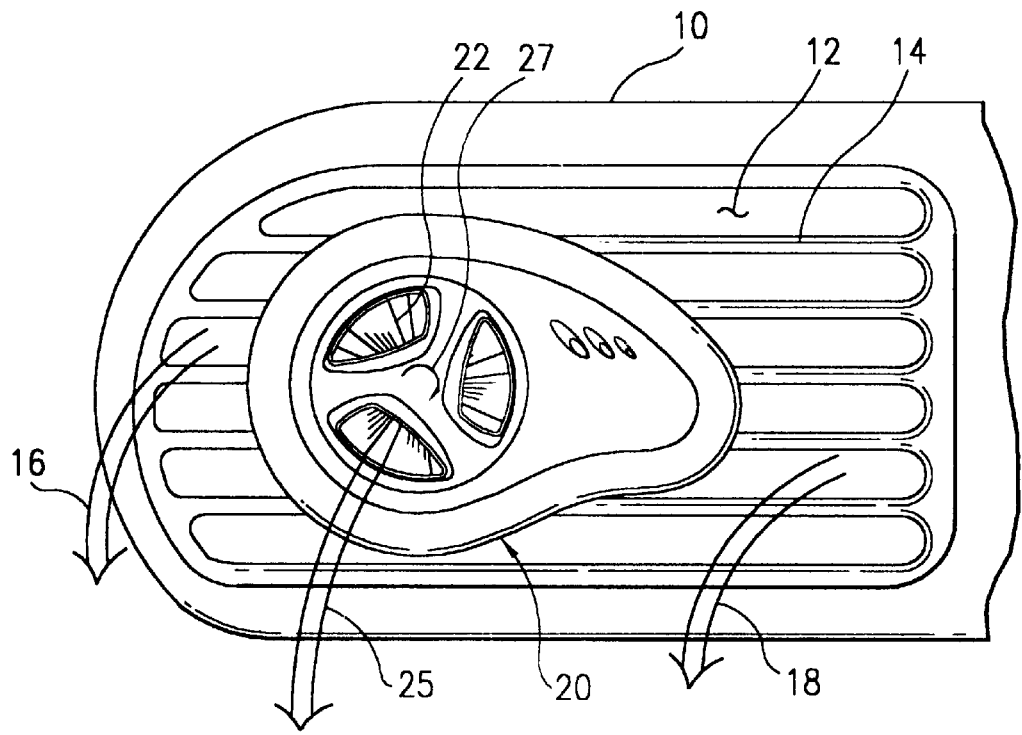
FIG. 1 diagrammatically illustrates the air freshener device with a fan or turbine mounted on a ventilation duct in accordance with the principles of the present invention.

FIG. 1 diagrammatically illustrates ventilation panel 10 or duct having a plurality of duct air passages 12 and ventilation vanes 14. Forced air, diagrammatically illustrated by arrows 16, 18, is expelled from ventilation duct 10. In a vehicle, commonly air conditioned or cooled air is expelled from ventilation duct 10. The air freshener device 20 includes, in its interior, a fan 22 and an air freshener pellet 24 (FIG. 2) which (a) causes arcuate air flow and rotatable air flow in the generally hollow interior of the housing and (b) freshens the air, mixes the freshened air with the expelled air and ejects that air from the housing as shown by arrow 25. Fan 22 rotates, in this embodiment, in a clockwise direction as shown by arrow 27.

Figure 2:
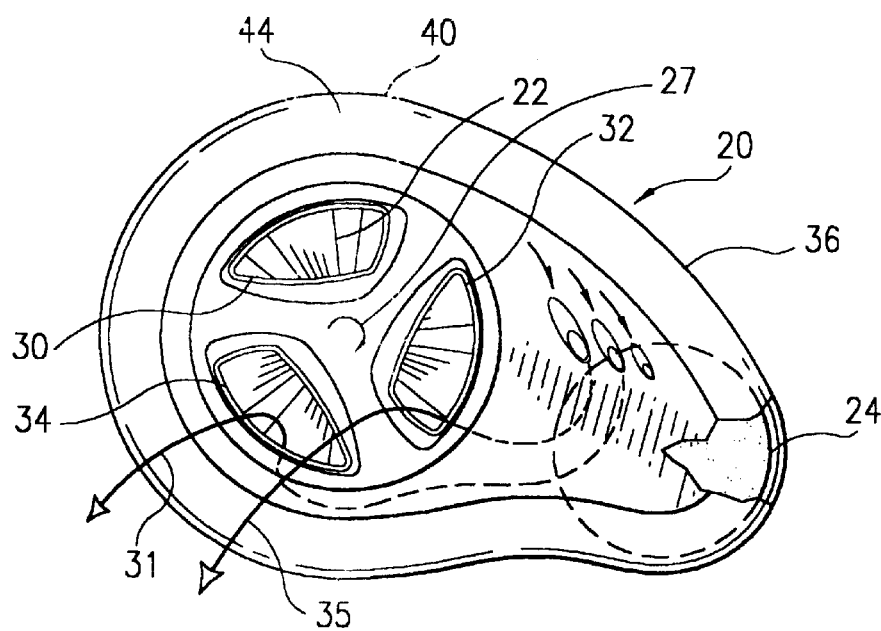
FIG. 2 is a detailed view of the air freshener device showing, in a partial, broken away view, the air freshener pellet.

FIG. 2 diagrammatically illustrates an enlarged version of air freshener device 20. Similar numerals designate similar items throughout the drawings. When the air is expelled from ventilation duct 10, the expelled air enters an input port in the back side of air freshener device 20, rotates fan 22 in direction 27, and causes both arcuate and, preferably, rotating air currents in the interior of air freshener device 20. These arcuate and circulating air currents pass over and around air freshener pellet 24. Air freshener pellet 24 discharges or off-gases scents or absorbs obnoxious fumes and generally freshens the air. This air flow is ejected from output air ports 30, 32 and 34 as shown by arrows 33, 35. Internal air flow inside housing 36 is shown by dash-dot-dash flow lines in FIG. 2. Of course, flow lines 33, 35 are only exemplary of the air flow. This air flow in the inside of air freshener device 20 may be considered chaotic or random. However, a reasonable amount of arcuate and circular air flow is created by rotatable fan 22 such that the air picks up the scent from air freshener pellet 24.

FIG. 3 diagrammatically illustrates an exploded rearward view of the air freshener device. In a preferred embodiment, housing 36 consists of a front clam shell member 40 and a rear clam shell member 42. Clam shell member 40 includes a front side 44 (FIG. 2). Rearward clam shell member 42 includes a back side 46. Back side 46 must have at least one input air port and, preferably, a plurality of input air ports. Input ports 48, 50 enable the air expelled from the ventilation duct 10 to impact rotatable fan 22. Rotatable fan 22 has a plurality of fan blades, one of which is fan blade 52. Blade 52 includes a leading air foil edge 54 and a trailing edge 56. Air expelled from the ventilation duct impacts the back side 58 of fan blade 52 and escapes between the circumferentially spaced apart fan blades. However, the air impacting the back side of trailing edge 56 is blocked and is forced into air gap 60. This causes fan 22 to rotate in the direction shown by arrow 62. The rotating fan causes arcuate and, in a preferred embodiment, rotating air within the hollow interior 70 formed by clam shell member 40 and clam shell member 42. Further, input air ports 72 and miniature or supplemental air foil shaped air ports 74 draw in air based upon the rotation of fan 22 and the force of the expelled air from the ventilation duct. Air foil shaped ports contribute to the arcuate air flow.

An air freshener pellet 24 is captured in pellet space 80 by retaining walls 82, 84. Pellet is spaced away from interior surface 86 of front clam shell member 40 by a spacing member 88. Rotating air caused by fan 22 and diagrammatically shown by arrow 67 and air drawn into input port 72 shown by arrow 69 arcuately flows over and rotatably flows around air freshener pellet 24 as shown by arrows 81 and 83. This air is expelled from air output ports 30, 32, 34 after being freshened.

As used herein, the term "pellet" is meant to cover the following air freshener devices.

Air Freshener Table scented pellet pellet which absorbs air fouling chemical compositions packet with air flow pockets which contain small pellets or beads of air freshener material sponge which can absorb and discharge liquid air freshener In a current embodiment, a solid scented pellet is utilized. However, a pellet which absorbs obnoxious or air fouling chemical compositions may be utilized. Further, a packet which holds small pellets or beads of air freshening material can be utilized. This packet should have air holes such as netting or other types of material. This packet could be placed in air freshener space 80 in the interior of housing 20. Further, a sponge which initially absorbs liquid air freshener and which discharges or permits that air freshener to evaporate could be utilized. In this manner, the user could simply drip liquid air freshener onto the sponge, close up the air freshener device and mount the device on vanes 14.

In a preferred embodiment, the air freshener device can be taken apart by opening and separating clam shell member 40 from clam shell member 42. The following table lists the mounts which could be used to assemble and disassemble the housing.

Housing Mounts interference fit male and female lip and ledge

U-shaped channel with female lip (tongue and groove)

screws and nuts or clip-fasteners tabs and capture channels straps hook and loop (VELCRO) fasteners It is commonly known that air freshener pellets or discharge units eventually become "stale" in that they no longer freshen air passing over and around those units. Accordingly, the user of the air freshener device of the present invention should be able to disassemble the device, insert a new air freshener pellet, quickly assemble the device and mount the device back on the ventilation duct.

In order to achieve smooth rotation of fan 20, that fan includes a fan hub 110, a small metal sleeve 112 which fits on stub 114. Hub 110 includes a hollow cylinder which fits over sleeve 112. Stub 114, in the present embodiment, extends from interior side 84 of clam shell member 40. However, the device could easily be reconfigured such that stub 114 extends from rearward clam shell member 42.

Retaining walls 82, 84 and stub 114 mate with corresponding surfaces (not shown) on the interior of rearward clam shell member 42. Further, these retaining walls and stub act as support spacers for the housing.

Arcuate air flow in the interior 70 of housing 20 is enhanced by arcuate wall surface 120 and 122.

In order to mount air freshener device 20 on the ventilation ducts, a number of mounting systems can be utilized. The ventilator mount table which follows provide some examples of these mounting systems.

Ventilator Mounts clips straps hook and loop (VELCRO) fasteners two-sided adhesive tape parallel, expanding clip with two lateral clip members (optional outboard teeth)

clip-on screw or nut with complementary screw or nut or clip-fasteners on housing In the present invention, a clip 140 (FIG. 4) has a back side tab 142 which slides, as shown by double headed arrow 144, into and out of channel 146. Clip 140 includes upper and lower clip members 150, 152. Upper and lower clip members 150, 152 expand apart such that they grip duct vane 14 shown in FIG. 1. It should be noted that the air freshener housing could be strapped on to the ventilator duct, a hook and loop or VELCRO fastener attachment can be utilized, two-sided adhesive tape can be utilized, expanding clips which, instead of capturing and compressing a single duct vane expand outboard from each other such that the clip expands and captures the upper and lower adjacent duct vanes. Further, screws and nuts could be utilized.

In order to enhance air flow, both arcuate and circular, housing 20 may include along side 170 one or more side ports 172, 174. The side ports 172, 174 are adjacent air freshener pellet 24 and pellet space 80 shown in FIG. 3.

The claims appended hereto are meant to cover modifications and changes within the scope and spirit of the present invention.

What is claimed is:

1. An air freshener device adapted to be mounted on a ventilation duct in a vehicle, said ventilation duct carrying forced air which is expelled from said ventilation duct, said air freshener device comprising:

a housing having a front side and a back side, said housing having air input and air output ports defined thereon;

means for mounting said housing to said ventilation duct disposed on said backside of said housing;

an air driven rotatable fan disposed in said housing intermediate said air input and said air output ports;

an air freshener pellet disposed within said housing at a fixed lateral position with respect to said fan and with respect to said air input and output ports; and an input scent airport adjacent said air freshener pellet and laterally disposed away from said fan air input port.

2. An air freshener device as claimed in claim 1 wherein said input air port is disposed on said backside of said housing and said housing has a substantially hollow interior.

3. An air freshener device as claimed in claim 2 wherein said output air port is disposed on said front side of said housing.

4. An air freshener device as claimed in claim 1 wherein said fan includes a plurality of fan blades and each fan blade includes a leading airfoil edge and a trailing airfoil edge, said trailing airfoil edge of each one of said plurality of fan blades disposed proximate said input air port on said backside of said housing.

5. An air freshener device as claimed in claim 1 wherein said input and output ports include a plurality of input air ports and a plurality of output air ports, said plurality of input ports disposed on said backside of said housing and said plurality of output air ports disposed on said front side of said housing.

6. An air freshener device as claimed in claim 5 wherein said fan includes a plurality of fan blades circumferentially disposed about a hub, and each fan blade includes a leading airfoil edge and a trailing airfoil edge, said trailing airfoil edge of each one of said plurality of fan blades disposed proximate at least one of said plurality of input air ports on said backside of said housing.

7. An air freshener device as claimed in claim 6 wherein said input scent air port is one of a plurality of scent input ports disposed adjacent said air freshener pellet and lateral with respect to said fan input port.

8. An air freshener device as claimed in claim 1 wherein said input air port is a primary input air port disposed on said backside of said housing next to said ventilation duct and said output air port is disposed on said front side of said housing, said housing having a substantially hollow interior, said air freshener pellet disposed in said hollow interior at a position lateral and offset from said primary input air port, said backside of said housing defining a supplementary input air port as said input scent air port adjacent said air freshener pellet.

9. An air freshener device as claimed in claim 8 wherein said fan includes a plurality of fan blades circumferentially disposed about a hub, and each fan blade includes a leading airfoil edge and a trailing airfoil edge, said trailing airfoil edge of each one of said plurality of fan blades disposed proximate at said primary input air port on said backside of said housing.

10. An air freshener device as claimed in claim 1 wherein said housing includes a front clamshell member and a rear clamshell member and includes means for removably mounting said front and rear clamshell members together.

11. An air freshener device as claimed in claim 9 wherein said housing includes a front clamshell member and a rear clamshell member and includes means for removably mounting said front and rear clamshell members together, said housing having a substantially hollow interior, one of said front and rear clamshell members having a stub disposed within said hollow interior of said housing, said fan hub movably mounted on said stub.

12. A method for freshening air flow expelled from a ventilation duct in a vehicle comprising the steps of:

providing a substantially hollow housing with air input and air output ports on opposite faces of said hollow body housing, said housing capturing an air freshener pellet at a fixed position therein;

providing a rotatable, air driven fan laterally disposed away from said air freshener pellet and rotatably mounted in said housing at a position spaced apart from said air freshener pellet;

mounting said housing on said ventilation duct within the expelled air flow and admitting air into said hollow housing via said air input port;

generating arcuate and laterally directed air flow within said housing and over said laterally disposed air freshener pellet at said fixed position laterally spaced apart from said air driven fan; and, ejecting freshened air with said arcuate air flow from said housing via said air output port.

13. The method as claimed in claim 12 including the step of rotating laterally directed air in a single plane over said air freshener pellet in said housing prior to ejecting said freshened air.

14. The method as claimed in claim 13 including the step of disassembling said housing and replacing said air freshener pellet with another air freshener pellet.

15. The method as claimed in claim 13 including the step of providing an input scent air port adjacent said air freshener pellet and laterally disposed away from said fan air input port in said housing, disposing said fan within said expelled air flow thereby generating said acuate air flow within said hollow housing, pulling air into said input scent air port and over said air freshener pellet and ejecting scented air from said air output port.

16. The method as claimed in claim 12 wherein the step of mounting said housing on said ventilation duct includes the step of removably mounting said housing thereon.

17. A method as claimed in claim 15 wherein the step of generating arcuate air flow within said housing includes the steps of admitting the ventilation duct expelled air flow into said housing at multiple locations including at said fan air input port and at said laterally disposed scent air input port, channeling interior air flow within said housing about said air freshener pellet by rotating said air flow normal to said expelled air and laterally directing the rotating air over said pellet and mixing said channeled, scented air flow with said rotating air flow prior to ejecting said freshened air from said housing.

18. An air freshener device adapted to be mounted on a ventilation duct, said ventilation duct carrying forced air which is expelled from said ventilation duct, said air freshener device comprising;

a housing having a front side and a backside, said housing having fan input and fan output air ports defined thereon;

means for mounting said housing to said ventilation duct disposed on said backside of said housing;

an air driven rotatable fan disposed in said housing intermediate and between said input and said output air ports, said fan defining a plane in said housing, said fan rotating in said plane; and an air freshener carrier disposed within said housing at a fixed position lateral to said air driven fan and in said plane defined by said fan.

19. An air freshener device as claimed in claim 18 wherein said air freshener carrier is one from the group of a scented pellet, a packet containing air freshener beads and a sponge which carries liquid air freshener.

20. An air freshener device as claimed in claim 19 wherein said fan includes a plurality of fan blades and each fan blade includes a leading airfoil edge and a trailing airfoil edge, said trailing airfoil edge of each one of said plurality of fan blades disposed proximate said input air port on said backside of said housing.

* * * * *